US00PP28630P3

(12) United States Plant Patent
Yamada

(10) Patent No.: US PP28,630 P3
(45) Date of Patent: Nov. 14, 2017

(54) ***CATHARANTHUS* PLANT NAMED 'SUNCATFE 43'**

(50) Latin Name: *Catharanthus roseus*
Varietal Denomination: Suncatfe 43

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 11 days.

(21) Appl. No.: 14/999,207

(22) Filed: Apr. 11, 2016

(65) Prior Publication Data

US 2017/0295691 P1 Oct. 12, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. A. Whealy

(57) ABSTRACT

A new and distinct cultivar of *Catharanthus* plant named 'Suncatfe 43', characterized by its compact, upright to outwardly spreading and uniformly mounding plant habit; vigorous growth habit; freely basal branching habit; freely flowering habit; long flowering period; relatively small star-shaped white-colored flowers; and good garden performance.

1 Drawing Sheet

Botanical designation: *Catharanthus roseus.*
Cultivar denomination: 'SUNCATFE 43'.

BACKGROUND OF THE INVENTION

The present invention relates to a new and distinct *Catharanthus* plant, botanically known as *Catharanthus roseus* and hereinafter referred to by the cultivar name 'Suncatfe 43'.

The new *Catharanthus* plant is a product of a planned breeding program conducted by the Inventor in Higashiomi, Shiga, Japan. The objective of the breeding program is to develop new compact and freely branching *Catharanthus* plants with numerous small flowers.

The new *Catharanthus* plant originated from a cross-pollination conducted by the Inventor in Higashiomi, Shiga, Japan in September, 2011 of a proprietary selection of *Catharanthus roseus* identified as code designation FS22-9, not patented, as the female, or seed, parent with a proprietary selection of *Catharanthus roseus* identified as code designation CL, not patented, as the male, or pollen, parent. The new *Catharanthus* plant was discovered and selected by the Inventor as a single flowering plant from within the progeny of the stated cross-pollination in a controlled greenhouse environment in Higashiomi, Shiga, Japan in September, 2013.

Asexual reproduction of the new *Catharanthus* plant by vegetative tip cuttings in a controlled greenhouse environment in Higashiomi, Shiga, Japan since December, 2013, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncatfe 43'. These characteristics in combination distinguish 'Suncatfe 43' as a new and distinct *Catharanthus* plant:

1. Compact, upright to outwardly spreading and uniformly mounding plant habit.
2. Vigorous growth habit.
3. Freely basal branching habit.
4. Freely flowering habit.
5. Long flowering period.
6. Relatively small star-shaped white-colored flowers.
7. Good garden performance.

Plants of the new *Catharanthus* can be compared to plants of the female parent selection. Plants of the new *Catharanthus* differ primarily from plants of the female parent selection in flower color as plants of the female parent selection have red-colored flowers.

Plants of the new *Catharanthus* can be compared to plants of the male parent selection. Plants of the new *Catharanthus* differ primarily from plants of the male parent selection in the following characteristics:

1. Plants of the new *Catharanthus* have smaller flowers than plants of the male parent selection.
2. Plants of the new *Catharanthus* and the male parent selection differ in flower color as plants of the male parent selection have lavender-colored flowers.

Plants of the new *Catharanthus* can be compared to plants of the *Catharanthus roseus* 'Suncatha 2460', disclosed in a U.S. Plant Pat. No. 27,455. In side-by-side comparisons, plants of the new *Catharanthus* differ from plants of 'Suncatha 2460' in the following characteristics:

1. Plants of the new *Catharanthus* are not as broad as plants of 'Suncatha 2460'.
2. Plants of the new *Catharanthus* have larger leaves than plants of 'Suncatha 2460'.

3. Plants of the new *Catharanthus* have broader flower petals than plants of 'Suncatha 2460'.
4. Plants of the new *Catharanthus* and 'Suncatha 2460' differ in flower color as plants of 'Suncatha 2460' have flowers that are light red purple in color with a distinct eye zone.
5. Plants of the new *Catharanthus* have longer sepals than plants of 'Suncatha 2460'.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet is a side perspective view of a typical flowering plant of 'Suncatfe 43' grown in a container.

The photograph at the bottom of the sheet is a close-up view of a typical flowering plant of 'Suncatfe 43'.

DETAILED BOTANICAL DESCRIPTION

The aforementioned photographs and following observations, measurements and values describe plants grown during the late summer/early autumn in 15-cm containers in an outdoor nursery in Higashiomi, Shiga, Japan and under cultural practices typical of commercial production. During the production of the plants, day temperatures averaged 25° C. and night temperatures averaged 15° C. Plants were six months old when the photographs were taken and seven months old when the description was taken. In the following description, color references are made to The Royal Horticultural Society Colour Chart, 2007 Edition, except where general terms of ordinary dictionary significance are used.

Botanical classification: *Catharanthus roseus* 'Suncatfe 43'.

Parentage:

*Female, or seed, parent*.—Proprietary selection of *Catharanthus roseus* identified as code designation FS22-9, not patented.

*Male, or pollen, parent*.—Proprietary selection of *Catharanthus roseus* identified as code designation CL, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to outwardly spreading and uniformly mounding plant habit; freely basal branching habit, about ten basal branches each with about four secondary branches developing per plant; vigorous growth habit.

*Plant height*.—About 26 cm.

*Plant diameter*.—About 50 cm.

Lateral branch description:

*Length*.—About 23 cm.

*Diameter*.—About 1.9 mm.

*Internode length*.—About 1.7 cm.

*Strength*.—Strong.

*Aspect*.—Upright to somewhat outwardly.

*Texture*.—Sparsely pubescent; rough.

*Color*.—Close to 145B.

Leaf description:

*Arrangement*.—Opposite, simple.

*Length*.—About 4.15 cm.

*Width*.—About 1.75 cm.

*Shape*.—Elliptic.

*Apex*.—Mucronate.

*Base*.—Cuneate.

*Margin*.—Entire.

*Texture, upper and lower surfaces*.—Pubescent; rough.

*Venation pattern*.—Pinnate; reticulate.

*Color*.—Developing leaves, upper surface: Close to 144A. Developing leaves, lower surface: Close to 144B. Fully expanded leaves, upper surface: Close to 138A; venation, close to 145C. Fully expanded leaves, lower surface: Close to 138B; venation, close to 145D.

*Petioles*.—Length: About 5.8 mm. Diameter: About 1.2 mm. Texture, upper and lower surfaces: Sparsely pubescent. Color, upper and lower surfaces: Close to 145D.

Flower description:

*Flower arrangement and habit*.—Single star-shaped salverform flowers arising from upper leaf axils; freely flowering habit with numerous small flowers developing per plant; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.6 cm. Diameter: About 3 mm. Shape: Ovoid to cylindrical. Color: Close to N155B.

*Flower diameter*.—About 2.7 cm.

*Flower length (depth)*.—About 2.6 cm.

*Tube length*.—About 2.4 cm.

*Tube diameter, proximally*.—About 1.1 mm.

*Tube diameter, distally*.—About 1.9 mm.

*Corolla*.—Arrangement: Five petals in a single whorl fused at the base into a tube. Petal length from throat: About 1.4 cm. Petal width: About 8.2 mm. Petal shape: Elliptic to broadly oblanceolate. Petal apex: Cuspidate. Petal margin: Entire. Petal texture, upper and lower surfaces: Smooth, glabrous. Throat texture: Smooth, glabrous. Tube texture: Pubescent. Color: Petal, when opening and fully opened, upper surface: Close to NN155C; faint stripe towards the throat, close to 73D. Petal, when opening and fully opened, lower surface: Close to NN155C. Throat:

Proximally, close to 145D; distally, close to 150C. Tube: Proximally, close to 36A; distally, close to 145B to 145C.

*Calyx*.—Arrangement: Star-shaped tubular calyx with five sepals fused towards the base. Sepal length: About 3.1 mm. Sepal width: About 0.9 mm. Sepal shape: Lanceolate. Sepal apex: Acuminate. Sepal margin: Entire. Sepal texture, upper and lower surfaces: Sparsely pubescent. Color, upper and lower surfaces: Close to 144B.

*Peduncles*.—Length: About 2 mm. Diameter: About 1 mm. Angle: Upright to outwardly. Strength: Strong. Texture: Sparsely pubescent. Color: Close to 145B.

*Reproductive organs*.—Stamens: Quantity per flower: Five. Anther size: About 1.6 mm by 0.8 mm. Anther shape: Narrowly elliptic. Anther color: Close to 158B. Pollen amount: Scarce. Pollen color: Close to 158D. Pistils: Quantity per flower: One. Pistil length: About 1.9 cm. Style color: Close to 145D. Stigma shape: Globose. Stigma color: Close to 145B. Ovary color: Close to 144C. Seeds and fruits: Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants.

It is claimed:

1. A new and distinct *Catharanthus* plant named 'Suncatfe 43' as illustrated and described.

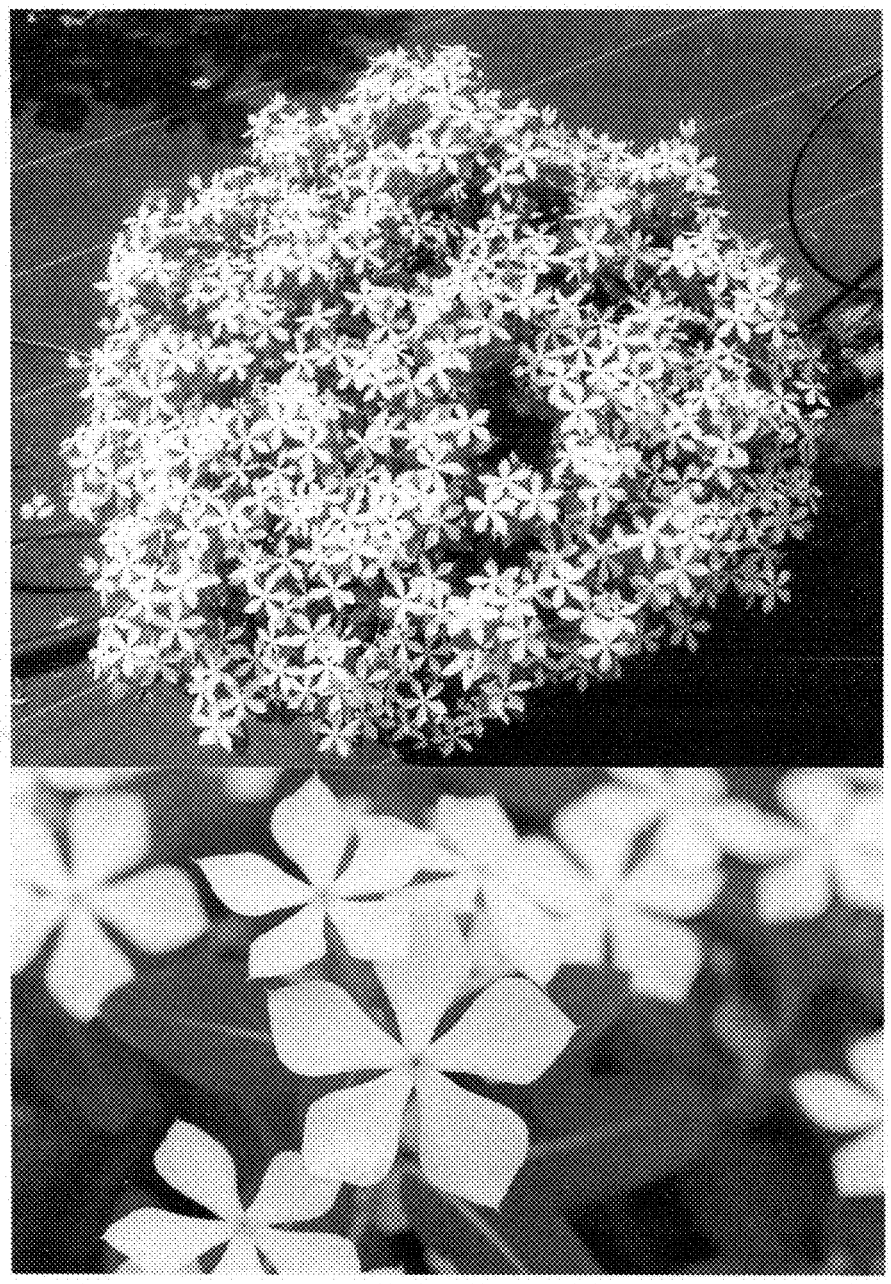

* * * * *